US010307623B2

(12) United States Patent
Cho

(10) Patent No.: US 10,307,623 B2
(45) Date of Patent: Jun. 4, 2019

(54) NASAL FILTER

(71) Applicant: Ted Cho, Los Angeles, CA (US)

(72) Inventor: Ted Cho, Los Angeles, CA (US)

( * ) Notice: Subject to any disclaimer, the term of this patent is extended or adjusted under 35 U.S.C. 154(b) by 490 days.

(21) Appl. No.: 15/246,192

(22) Filed: Aug. 24, 2016

(65) Prior Publication Data

US 2018/0056099 A1 Mar. 1, 2018

(51) Int. Cl.

| | |
|---|---|
| ***A62B 23/00*** | (2006.01) |
| ***A61M 15/08*** | (2006.01) |
| ***A61M 16/06*** | (2006.01) |
| ***A62B 23/06*** | (2006.01) |
| ***A62B 25/00*** | (2006.01) |

(52) U.S. Cl.

CPC .............. *A62B 23/06* (2013.01); *A62B 25/00* (2013.01)

(58) Field of Classification Search

CPC . A44C 15/0065; A47F 11/10; A61B 17/0401; A61B 17/8685; A61B 2017/0408; A61B 2017/0409; A61B 2017/0414; A61B 2017/042; A61B 2017/0425; A61F 2/0805; A61F 2/0811; A61F 2002/0888; A61M 15/08; A61M 15/085; A62B 23/06; B08B 1/04; B26D 3/08; B26D 3/10; B26F 1/02; B26F 1/3846; C07D 213/75; C07D 471/04; C12C 3/12; C12C 5/026; C12C 9/025; F16B 13/061; F21V 33/0012; F21W 2131/301; F21W 2131/405; F21Y 2115/10; G06Q 10/06; H01L 21/02087; H01L 21/67046; H01L 21/67051; Y10T 137/7303

See application file for complete search history.

(56) References Cited

U.S. PATENT DOCUMENTS

| | | | | |
|---|---|---|---|---|
| 2,777,442 A * | 1/1957 | Zelano | A44C 15/0065 | 128/206.11 |
| 7,918,225 B2 * | 4/2011 | Dolezal | A62B 23/06 | 128/205.27 |
| 8,020,700 B2 * | 9/2011 | Doshi | B26F 1/02 | 128/200.24 |
| 2006/0016450 A1 * | 1/2006 | Pearson | A62B 23/06 | 128/206.11 |
| 2007/0062538 A1 * | 3/2007 | Foggia | A61M 15/08 | 128/207.18 |

* cited by examiner

*Primary Examiner* — Annette Dixon

(74) *Attorney, Agent, or Firm* — John K. Park; Park Law Firm

(57) ABSTRACT

A nasal filter is provided, including first and second rim portions, first and second crease portions, and a bridge portion. The first or second rim portion has a shape configured for contacting and being latched on a perimeter of a user's nostril. The first or second crease portion is provided in the first or second rim portion, and the first or second crease portion comprises concentric ring-shaped creases and collapsed into a plane defined by the first or second rim portion when flattened and deployed into a conic or circular pyramid shape configured to fit in the user's nostril when pressed perpendicularly to the plane. The bridge portion connects the first rim portion to the second rim portion. The nasal filter is configured to be deployed into the user's nostrils and to provide a filtering of breathed-in air.

16 Claims, 3 Drawing Sheets

NASAL FILTER

BACKGROUND OF THE INVENTION

The present invention relates to a nasal filter.

Air pollution becomes a serious problem in this world full of burning of fossil fuels in a gigantic and accelerating speed nowadays. The internal combustion engines, factories, and other air-polluting products or cultures in a human scale such as smoking are the sources of dust, fine dust, etc.

Protection from such pollutants is one of major issues in the health or environment community.

Personal protection gears have been suggested in the corresponding industry, but there are many issues to improve.

The invention suggests a new approach to solve the above problems of the prior arts.

Accordingly, a need for a nasal filter has been present for a long time considering the expansive demands in the everyday life. This invention is directed to solve these problems and satisfy the long-felt need.

SUMMARY OF THE INVENTION

The present invention contrives to solve the disadvantages of the prior art.

An object of the invention is to provide a nasal filter, which can be used personally and can be worn very conveniently.

Another object of the invention is to provide a nasal filter, which can provide the maximized protection by maximizing its filtering surface inside of the nostril.

An aspect of the invention provides a nasal filter, comprising a first rim portion, a first crease portion, a second rim portion, a second crease portion, and a bridge portion.

The first rim portion has a shape configured for contacting and being latched on a perimeter of the user's nostril.

The first crease portion is provided in the first rim portion, and the first crease portion comprises a plurality of concentric ring-shaped creases and collapsed into a first plane defined by the first rim portion when flattened and deployed into a conic or circular pyramid shape configured to fit in the user's nostril when pressed perpendicularly to the first plane.

The second rim portion has a shape configured for contacting and being latched on a perimeter of the other nostril of the user.

The second crease portion is provided in the second rim portion, and the second crease portion comprises a plurality of concentric ring-shaped creases and collapsed into a second plane defined by the second rim portion when flattened and deployed into a conic or circular pyramid shape configured to fit in the user's nostril when pressed perpendicularly to the second plane.

The bridge portion connects the first rim portion to the second rim portion.

The nasal filter is configured to be deployed into the user's nostrils and to provide a filtering of breathed-in air.

The first and second rim portions may be thicker than the first and second crease portions, respectively.

Each of the rim portions and the crease portions may have a color coded for properties of the nasal filter including effectiveness, enhancement, and flavor.

Each of the first and second rim portions may have substantially a shape of circle, ellipse, or rectangle.

Each of the first and second crease portions may have at least four (4) concentric ring-shaped creases. Actually, the number of ring-shaped creases can be selected for a specific design of the nasal filter. Their numbers and exact dimensions can be chosen for maximizing the filtering area.

The bridge portion may comprise one or more creases for facilitating to adjust a width thereof.

The nasal filter may further comprise a first folding holder portion and a second folding holder portion.

The first folding holder portion is attached to an outer end of the first rim portion, comprises a horizontal part and a vertical part extending from the horizontal perpendicularly, and is configured for holding a perimeter of the user's nostril.

The second folding holder portion is attached to an outer end of the second rim portion, comprises a horizontal part and a vertical part extending from the horizontal perpendicularly, and is configured for holding a perimeter of the other nostril of the user.

Each of the first and second folding holder portions may be adapted to be flattened or bent and held in a specific shape.

The nasal filter may further comprise a filter container made of a plate having a recess with a shape of the nasal filter adapted to receive the nasal filter.

The recess of the filter container may have a substantially same thickness as the first or second rim portion.

The nasal filter may further comprise a top sheet cover portion to be applied to and cover a top side of the filter container with the nasal filter received in the recess.

Each of the first and second folding holder portions 19, 29 may comprise a plurality of impressions configured for bending, so that each of the first and second folding holder portions 19, 29 can be bent, forming the horizontal and vertical parts described in the above.

The top sheet cover portion may be detachable.

The advantages of the present invention are: (1) the nasal filter according to the invention has a simple structure, enabling very powerful filter against air pollution; (2) the nasal filter according to the present invention is easy to put on and use; (3) One size fits all without any other assistant material; and (4) There is no chemical adhesive needed to adjust fitting the filter to or inside the nostrils.

Although the present invention is briefly summarized, the fuller understanding of the invention can be obtained by the following drawings, detailed description and appended claims.

BRIEF DESCRIPTION OF THE DRAWINGS

These and other features, aspects and advantages of the present invention will become better understood with reference to the accompanying drawings, wherein.

DETAILED DESCRIPTION EMBODIMENTS OF THE INVENTION

Referring to the figures, the embodiments of the invention are described in detail.

FIGS. 1 through 7 show nasal filters according to embodiments of the present invention.

Figure 1:
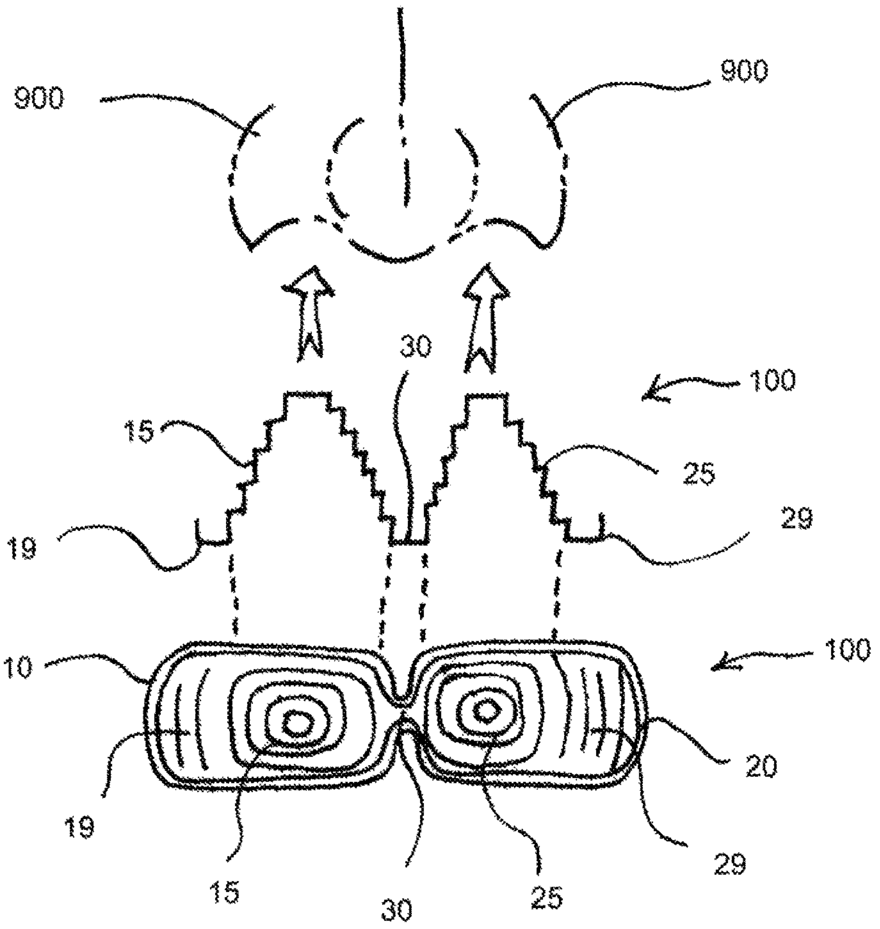
FIG. 1 shows a cross-sectional view and a top plan view of a nasal filter according to an embodiment of the invention.

An aspect of the invention provides a nasal filter 100, comprising a first rim portion 10, a first crease portion 15, a second rim portion 20, a second crease portion 25, and a bridge portion 30 as shown in FIG. 1.

The first rim portion 10 has a shape configured for contacting and being latched on a perimeter of nostril of the user's nose 900 as shown in FIG. 1.

Figure 2:
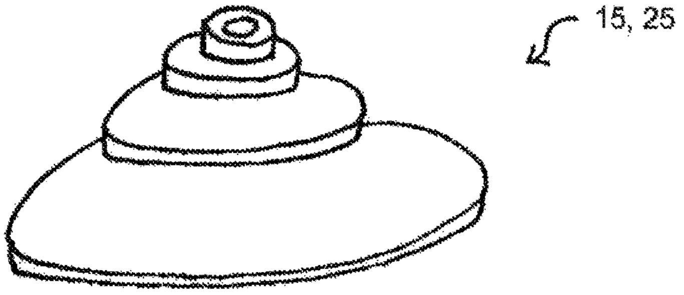
FIG. 2 shows a conceptual perspective view of a first crease portion deployed according to an embodiment of the invention.

The first crease portion 15 is provided in the first rim portion 10, and the first crease portion 15 comprises a plurality of concentric ring-shaped creases and collapsed into a first plane defined by the first rim portion 10 when flattened and deployed into a conic or circular pyramid shape configured to fit in the user's nostril when pressed perpendicularly to the first plane as shown in FIGS. 1 and 2.

The second rim portion 20 has a shape configured for contacting and being latched on a perimeter of the other nostril of the user.

The second crease portion 25 is provided in the second rim portion 20, and the second crease portion 25 comprises a plurality of concentric ring-shaped creases and collapsed into a second plane defined by the second rim portion when flattened and deployed into a conic or circular pyramid shape configured to fit in the user's nostril when pressed perpendicularly to the second plane as shown in FIGS. 1 and 2.

The bridge portion 30 connects the first rim portion 10 to the second rim portion 20.

The nasal filter 100 is configured to be deployed into the user's nostrils and to provide a filtering of breathed-in air as shown in FIG. 1.

The first and second rim portions 10, 20 may be thicker than the first and second crease portions 15, 25, respectively. However, in certain embodiments of the invention, the first and second rim portions 10, 20 may have same thickness as the first and second crease portions 15, 25.

Each of the rim portions 10, 20 and the crease portions 15, 25 may have a color coded for properties of the nasal filter 100 including effectiveness, enhancement, and flavor. Thus, the user may know the various kinds of the nasal filter by the color. The nasal filter may be impregnated with a specific texture, fragrance, etc. Sometimes the color may give a clue of the material of which the nasal filter is made.

Each of the first and second rim portions 10, 20 may have substantially a shape of circle, ellipse, or rectangle. In the illustrated embodiments, the first and second rim portions 10, 20 have rectangular shape. Of course, the shapes can be mixed in a nasal filter 100 as long as they can be deployed into a conic or pyramid shape or any shape which can fit in the nostrils.

Figure 3:
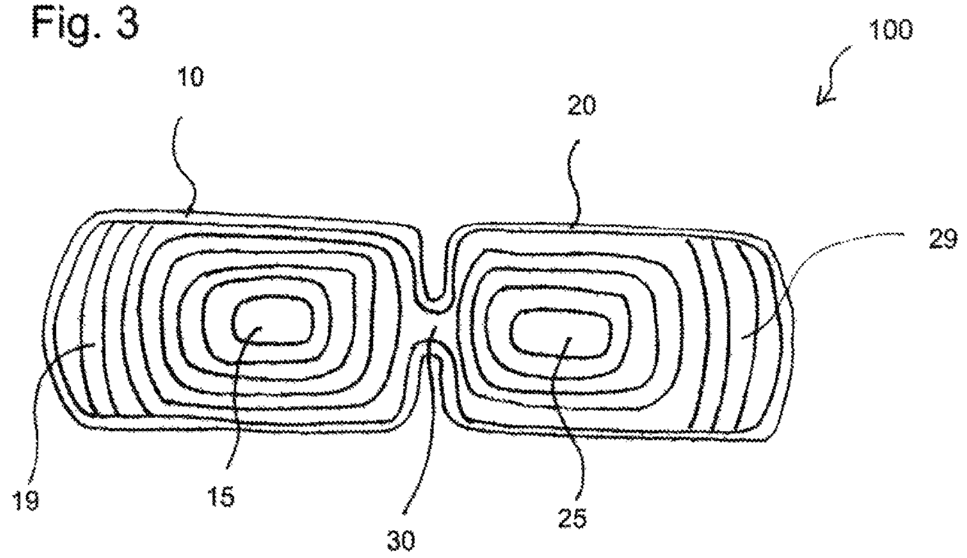
FIG. 3 shows a top plan view of a nasal filter according to an embodiment of the invention.

Each of the first and second crease portions 15, 25 may have at least four (4) concentric ring-shaped creases as shown in FIG. 3. However, the number of creases is not limiting in any case. The exact number of creases may depend on the pitch of the creases and even of the material thereof.

Figure 5:
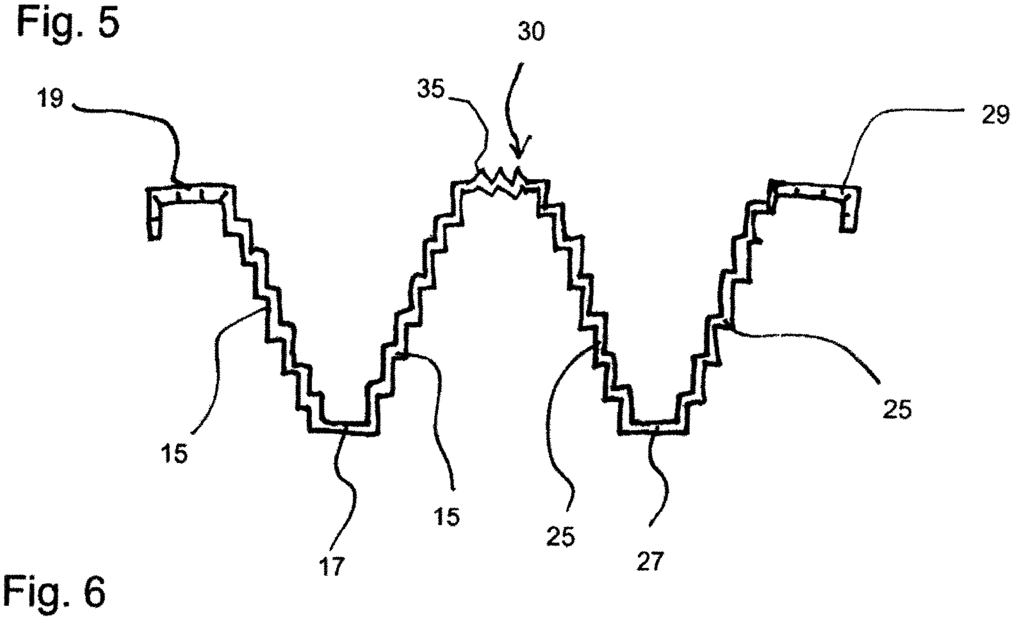
FIG. 5 shows a cross-sectional view of a nasal filter with a crease portion deployed according to an embodiment of the invention.

The bridge portion 30 may comprise one or more creases 35 for facilitating to adjust a width thereof as shown in FIG. 5. With the one or more creases 35, the nasal filter 100 may accommodate more easily for different users.

The nasal filter 100 may further comprise a first folding holder portion 19 and a second folding holder portion 29 as shown in FIGS. 1, 3, 5, and 6.

The first folding holder portion 19 is attached to an outer end of the first rim portion 10, comprises a horizontal part and a vertical part extending from the horizontal perpendicularly especially when deployed, and is configured for holding a perimeter of the user's nostril. However, sometimes the distinction between the crease portions 15, 25 and the folding holder portions 19, 29 is not so obvious. They may form a crease portion together as shown in FIGS. 1, 3, and 5.

Likewise, the second folding holder portion 29 is attached to an outer end of the second rim portion 20, comprises a horizontal part and a vertical part extending from the horizontal perpendicularly, and is configured for holding a perimeter of the other nostril of the user.

Each of the first and second folding holder portions may be adapted to be flattened or bent and held in a specific shape.

Figure 4:
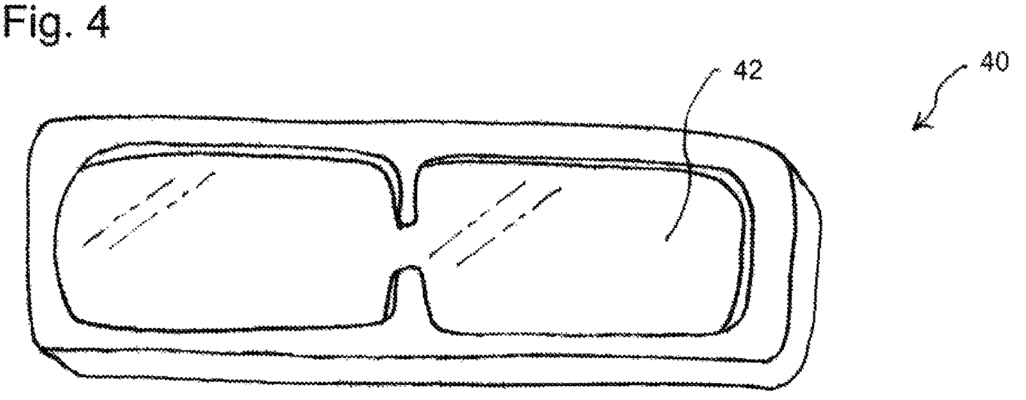
FIG. 4 shows a perspective view of a filter container for a nasal filter according to an embodiment of the invention.

The nasal filter 100 may further comprise a filter container 40 made of a plate having a recess 42 having a shape of the nasal filter 100 adapted to receive the nasal filter 100 as shown in FIGS. 3 and 4.

The recess 42 of the filter container 40 may have a substantially same thickness as the first or second rim portion 10, 20.

Figure 7:
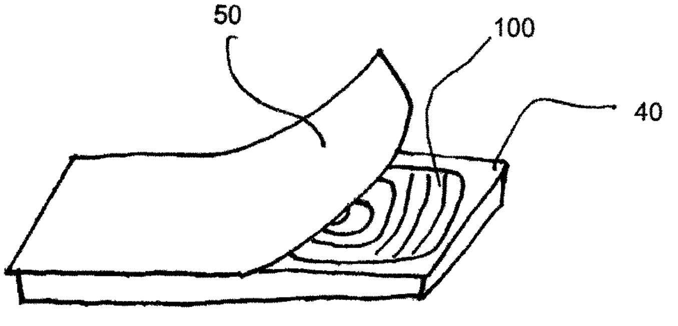
FIG. 7 shows a perspective view of a nasal filter packaged in a filter container according to an embodiment of the invention.

The nasal filter 100 may further comprise a top sheet cover portion 50 to be applied to and cover a top side of the filter container 40 with the nasal filter 100 received in the recess 42 as shown in FIG. 7.

The top sheet cover portion 50 may be detachable.

The rim portions 10, 20 and the crease portions 15, 25 are made of filtering material such as filtering paper. In certain embodiments of the invention, the crease portions 15, 25 only may be made of filtering material.

Referring to FIG. 1, the flat mesa portion at the top of the crease portions 15, 25 may be provided with a pointed structure with another crease, which may contribute more filtering area as discussed in the above.

Referring to FIG. 4, the recess 42 has a bottom floor blocking the bottom side thereof, which was indicated by double dashed lines on the bottom and by the differences between the depth of the recess 42 and the thickness of the filter container 40.

Figure 6:
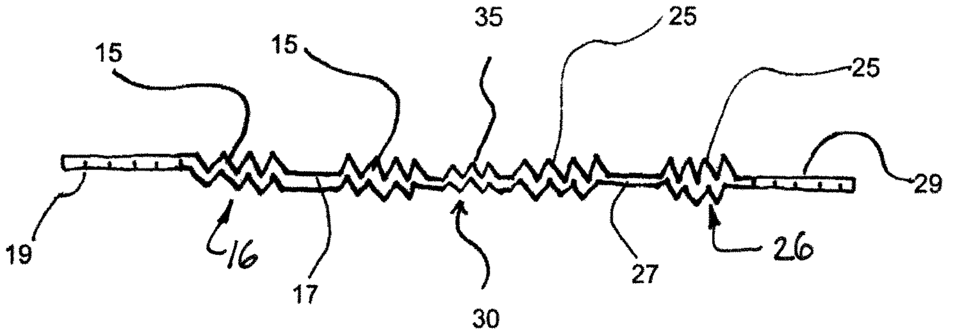
FIG. 6 shows a cross-sectional view of a nasal filter with a crease portion flattened according to an embodiment of the invention.

Each of the first and second folding holder portions 19, 29 may comprise a plurality of impressions configured for bending as shown in FIGS. 5 and 6, so that each of the first and second folding holder portions 19, 29 can be bent as shown in FIG. 5, forming the horizontal and vertical parts described in the above.

While the invention has been shown and described with reference to different embodiments thereof, it will be appreciated by those skilled in the art that variations in form, detail, compositions and operation may be made without departing from the spirit and scope of the invention as defined by the accompanying claims.

What is claimed is:

1. A nasal filter comprising:

a first rim portion having a shape configured for contacting and being latched on a perimeter of a user's nostril;

a first crease portion provided in the first rim portion, the first crease portion comprising a plurality of concentric ring-shaped creases in increasing diameter and collapsed flatly for storage into a first plane defined by the first rim portion and deployed into a conic or circular pyramid shape configured to fit in the user's nostril when pressed perpendicularly to the first plane;

a second rim portion having a shape configured for contacting and being latched on a perimeter of the other nostril of the user;

a second crease portion provided in the second rim portion, the second crease portion comprising a plurality of concentric ring-shaped creases in increasing diameter and collapsed flatly for storage into a first plane defined by the first rim portion and deployed into a conic or circular pyramid shape configured to fit in the user's nostril when pressed perpendicularly to the second plane; and a bridge portion connecting the first rim portion to the second rim portion, wherein the nasal filter is configured to be deployed into the user's nostrils and to provide a filtering of breathed-in air.

2. The nasal filter of claim 1, wherein the plurality of concentric ring-shaped creases of the first crease portion form a first wave pattern with same amplitude up and down from the first plane when stored and the plurality of concentric ring-shaped creases of the second crease portion form a second wave pattern with same amplitude up and down from the first plane when stored.

3. The nasal filter of claim 2, wherein the first wave pattern and the second wave pattern are the same.

4. The nasal filter of claim 2, wherein the first wave pattern and the second wave pattern are the different.

5. The nasal filter of claim 1, wherein each of the rim portions and the crease portions has a color coded for properties of the nasal filter including effectiveness, enhancement, and flavor.

6. The nasal filter of claim 1, wherein each of the first and second rim portions has substantially a shape of circle, ellipse, or rectangle.

7. The nasal filter of claim 1, wherein each of the first and second crease portions has at least four (4) concentric ring-shaped creases.

8. The nasal filter of claim 1, wherein the bridge portion comprises one or more creases for facilitating to adjust a width thereof.

9. The nasal filter of claim 2, further comprising:

a first folding holder portion, located at an outer end of the first rim portion, comprising a plurality of creases configured for each crease bending selectively forming a horizontal part and a vertical part extending from the horizontal perpendicularly to securely fit the nose of the user, and configured for holding a perimeter of the user's nostril; and a second folding holder portion, located at an outer end of the second rim portion, comprising a plurality of creases configured for each crease bending selectively forming a horizontal part and a vertical part extending from the horizontal perpendicularly to securely fit the nose of the user, and configured for holding a perimeter of the other nostril of the user.

10. The nasal filter of claim 9, wherein each of the first and second folding holder portions is adapted to be flattened or bent and held in a specific shape.

11. The nasal filter of claim 9, wherein the first wave pattern and the second wave pattern are the same.

12. The nasal filter of claim 9, wherein the first wave pattern and the second wave pattern are the different.

13. The nasal filter of claim 1, further comprising a filter container made of a plate having a recess with a shape of the nasal filter adapted to receive the nasal filter.

14. The nasal filter of claim 13, further comprising a top sheet cover portion to be applied to and cover a top side of the filter container with the nasal filter received in the recess.

15. The nasal filter of claim 14, wherein the top sheet cover portion is detachable.

16. The nasal filter of claim 1, wherein the rim portions and the crease portions are made of filtering material such as filtering paper.

* * * * *